United States Patent
Fernández Fernández et al.

(10) Patent No.: US 12,264,911 B2
(45) Date of Patent: Apr. 1, 2025

(54) DEVICE AND METHOD FOR CHARACTERISING THE ROUGHNESS PROFILE OF A TISSUE SAMPLE

(71) Applicant: Universidad Carlos III De Madrid, Leganés (ES)

(72) Inventors: Roberto Fernández Fernández, Leganés (ES); Jorge Ripoll Lorenzo, Leganés (ES); Asier Marcos Vidal, Leganés (ES)

(73) Assignee: Universidad Carlos III De Madrid, Leganés (ES)

( * ) Notice: Subject to any disclaimer, the term of this patent is extended or adjusted under 35 U.S.C. 154(b) by 276 days.

(21) Appl. No.: 17/906,143

(22) PCT Filed: Mar. 16, 2021

(86) PCT No.: PCT/ES2021/070192
§ 371 (c)(1),
(2) Date: Nov. 21, 2022

(87) PCT Pub. No.: WO2021/180998
PCT Pub. Date: Sep. 16, 2021

(65) Prior Publication Data
US 2023/0112077 A1    Apr. 13, 2023

(30) Foreign Application Priority Data

Mar. 12, 2020 (ES) ................ ES202030210

(51) Int. Cl.
*G01B 11/30* (2006.01)
*A61B 5/00* (2006.01)
*G01N 33/483* (2006.01)

(52) U.S. Cl.
CPC ............ *G01B 11/303* (2013.01); *G01B 11/30* (2013.01); *A61B 5/00* (2013.01); *G01N 33/4833* (2013.01)

(58) Field of Classification Search
CPC .. G01B 11/303; G01B 11/30; G01B 9/02094; A61B 5/00; A61B 5/0059; G01N 33/4833; G01N 2021/217; G01N 21/21; G01P 5/26
See application file for complete search history.

(56) References Cited

U.S. PATENT DOCUMENTS

| | | | | |
|---|---|---|---|---|
| 2004/0190002 A1* | 9/2004 | Schulte | ............. | G01B 9/02072 356/512 |
| 2012/0296576 A1* | 11/2012 | Shibata | ................ | G01B 11/303 702/40 |
| 2018/0023947 A1* | 1/2018 | Meng | .................. | G01B 11/303 348/46 |

FOREIGN PATENT DOCUMENTS

| | | |
|---|---|---|
| CN | 101694369 A | 4/2010 |
| WO | 2019/212959 A1 | 11/2019 |

OTHER PUBLICATIONS

International Search Report issued for International Patent Application No. PCT/ES2021/070192, dated Jun. 28, 2021 in 6 pages.
(Continued)

*Primary Examiner* — Michelle M Iacoletti
*Assistant Examiner* — Judy Dao Tran
(74) *Attorney, Agent, or Firm* — Knobbe, Martens, Olson & Bear, LLP (57) ABSTRACT

The invention describes a device (1) for characterizing the rough profile of a tissue sample comprising: a laser source (2) that illuminates the surface (100) of the tissue; a photodetector (3) that receives the light backscattered by the surface (100) of the tissue; and further a displacement means (4) configured to alternate between a first position wherein
(Continued)

a rotating ground glass (5) is disposed within the path of the laser beam towards the surface (100), a second position wherein a rotating half wave blade (6) is disposed within the path of the laser beam towards the surface (100); and a third position wherein within the path of the laser beam towards the surface (100) neither the ground glass plate (5) nor the half wave blade (6) are arranged, or the half wave blade (6) is arranged in a fixed non-rotating position.

11 Claims, 3 Drawing Sheets

(56) References Cited

OTHER PUBLICATIONS

Lee et al., "Noninterferometric wide-filed optical profilometry with nanometer depth resolution"; Optics Letters, vol. 27, N. 20, pp. 1773-1775 (2002).

* cited by examiner

DEVICE AND METHOD FOR CHARACTERISING THE ROUGHNESS PROFILE OF A TISSUE SAMPLE

CROSS-REFERENCE TO RELATED APPLICATIONS

This application is the U.S. National Phase under 35. U.S.C. § 371 of International Application PCT/ES2021/070192, filed Mar. 16, 2021, which claims priority to Spanish Patent Application No. P202030210, filed Mar. 12, 2020. The disclosures of the above-described applications are hereby incorporated by reference in their entirety.

OBJECT OF THE INVENTION

The invention generally belongs to the field of optics, and more particularly to the field of microscopy.

A first object of the present invention is a device designed to obtain useful information for the characterization of rough tissue samples.

A second object of the invention is a procedure carried out by said device to determine the degree of anisotropy of the sample through depolarization correlation measurements.

A third object of the invention is a procedure carried out by said device to determine the roughness frequency of the sample through speckle interferometry correlation measurements.

A fourth object of the invention is a procedure carried out by said device to determine the average speed of the dispersive components of the tissue through temporal correlation measurements.

BACKGROUND OF THE INVENTION

In the field of medicine, it is often necessary to determine the morphological characteristics of a certain tissue of a patient. In general, a biological tissue can be defined as a natural biological material made up of a complex and organized set of cells regularly distributed and endowed with a coordinated physiological behavior.

Currently, to obtain the mentioned information it is necessary to perform a biopsy. A biopsy procedure basically consists of the removal of a sample of the target tissue and the subsequent exhaustive study of the sample under a microscope by a pathologist. The results of this study are communicated to the doctor for evaluation and subsequent communication to the patient.

This method has the drawback that it requires a large amount of time, since the pathologist must carry out an individualized manual study of each of the samples to be studied. In addition, the high specificity of the training required to carry out the study of the sample under the microscope restricts the number of professionals suitable for this work. As a consequence, a waiting list is frequently generated in which the average time for the doctor to receive the results can be several weeks.

Ultimately, there is a need in this field for methods that are faster, simpler and cheaper.

DESCRIPTION OF THE INVENTION

The present invention solves the previous problem through the use of a new device attachable to a microscope that allows obtaining different types of measurements based on the light scattered in reflection, or light backscattered, by the tissue in response to its illumination by a laser source.

Indeed, the light scattered by reflection obtained through the microscope can be analyzed automatically using a suitable processing means, so that the final result is representative parameters of the surface of the tissue. The values of these parameters allow us to infer a large amount of useful information for the pathological diagnosis of the tissue sample in question.

As previously mentioned in this document, this new device is applicable to the analysis of biological tissue samples, such as samples obtained from a biopsy or the like, or even biological tissues in vivo. However, its application is not limited to biological tissues, but can be used in a general way for the characterization of any rough surface.

A first aspect of the invention is directed to a device for characterizing the rough profile of a tissue sample, which basically comprises the following elements: a laser source, a photodetector, and a displacement means. Each of these elements is described in more detail below:

a) Laser source

This is a laser source that illuminates the surface of the tissue with a continuous wave laser beam. The laser source, therefore, is oriented towards the surface of the tissue, so that the laser beam illuminates it.

In principle, any type of laser source can be used, although it is preferable that its wavelength does not exceed 635 nm, to avoid introducing subcutaneous information in the measurement.

b) Photodetector

The function of the photodetector is to receiving the light scattered in reflection by the surface of the tissue illuminated by the laser beam. To do this, the photodetector is located in a position wherein it receives the light scattered in reflection from the surface.

c) Displacement means

The displacement means is configured to alternate between various positions corresponding to the interposition of certain elements in the path of the laser beam in order to alter its characteristics before it reaches the surface. More specifically, the displacement means alternates between three positions:

A first position wherein a rotating ground glass plate is arranged within the path of the laser beam towards the surface. Thus, when the displacement means is in this position, the laser light passes through the ground glass plate and, as a consequence, the illumination pattern on the sample changes periodically depending on the angle of rotation of the ground glass plate.

As described in detail later in this document, this set-up allows for speckle interferometry correlation measurements to obtain a parameter called "roughness frequency".

A second position wherein a rotating half wave blade is arranged within the path of the laser beam towards the surface. In this way, when the laser beam passes through the half wave blade, the polarization of the laser beam that illuminates the sample rotates depending on the angle of rotation of the half wave blade.

As described in detail later in this document, this set-up makes it possible to check the polarization anisotropy of the sample by obtaining a parameter called "degree of depolarization".

A third position wherein neither the ground glass plate nor the half wave blade are arranged within the path of the laser beam towards the surface, or else the half wave blade is arranged in a fixed non-rotating position. Therefore, in this third position, the characteristics of the laser light reaching the surface remain constant over time.

As described in greater detail later in this document, this setup allows in-vivo dynamic information about the tissue to be obtained by obtaining a parameter called the average speed of the dispersive components of the tissue.

In principle, the displacement means can be implemented in any way as long as it allows switching between the three positions described above. For example, according to a preferred embodiment of the invention, the displacement means comprises:

i) Guide

The guide is arranged in front of the laser source perpendicular to the emitted laser beam. It can be, for example, a horizontal metal bar traversed perpendicular to the direction of the emitted laser beam.

ii) Frame

The frame is movable along the guide, the ground glass plate and the half wave blade being coupled to said frame.

This can be done in different ways. For example, the frame can take the form of a sliding carriage along the guide, so that it can take at least the three positions described previously in this document: in a first position of the carriage along the frame, the ground glass plate is located within the path of the laser beam at the same time it rotates; in a second position of the carriage along the frame, the half wave blade is located within the path of the laser beam at the same time it rotates; and in a third position of the carriage along the frame, neither the ground glass plate nor the half wave blade are located within the path of the laser beam, or else the half wave blade is located in a fixed position.

iii) Translation motor

The translation motor moves the frame along the guide to selectively place the ground glass plate, the half wave blade, or neither in the path of the laser beam.

In principle, any mechanical configuration capable of performing this function can be used. For example, the translation motor can be located at one end of the guide and connected to the frame through, for example, a belt driven by a pulley or the like. Alternatively, the guide itself can be a threaded bar which, when rotated by the translation motor, causes the carriage to move along it.

iv) Rotation motor

The rotation motor is coupled to the ground glass plate and half wave blade to respectively rotate the ground glass plate and half wave blade when facing the laser source.

This can be achieved in different ways. However, according to a preferred embodiment of the invention, the ground glass plate is attached to a first toothed wheel and the half wave blade is attached to a second toothed wheel. The rotation motor is coupled to said first and second toothed wheels to rotate them, for example by means of at least one third toothed wheel meshed with said first and second toothed wheels.

This novel device thus allows carrying out the aforementioned surface characterization procedures, since it allows selectively inserting the ground glass plate or the half wave blade in the path of the laser beam, as well as selectively rotating each of these elements depending on the position.

In preferred embodiments of the invention, the device further comprises optical light conducting means which conduct the laser beam from the laser source towards the surface of the tissue and the light scattered in reflection by the surface of the tissue towards the photodetector. In this way, it is not strictly necessary that the laser beam is emitted directly in a straight line towards the surface, but it is possible to use the optical means to guide it according to a path chosen according to the needs of each application.

For example, in one configuration, the optical light conducting means comprises mirrors, lenses and beam splitters. This configuration is especially suitable for the implementation of the device of the invention in a microscope, as it allows the insertion within the same optical path of other light signals such as a white light to illuminate the field of view, as well as the extraction of said optical path of light signals of interest.

In an alternative configuration, the optical light conducting means comprises an optical fiber housed in an endoscope. This configuration is especially suitable for use of the device in in vivo tissue analysis.

In principle, the analysis of the signals received by the photodetector to calculate the representative parameters of the surface of the tissue can be performed by a suitable external processing means. For example, the data obtained by the photodetector can be transmitted to a computer, tablet, smartphone, or any other similar device wherein dedicated software obtains said parameters. Alternatively, in another preferred embodiment of the present invention, the device itself comprises a processing means that receives the signal obtained by the photodetector in response to the light reflected in received dispersion and calculates said useful parameters for characterizing the rough profile of the surface.

According to a further preferred embodiment of the invention, the device is attached to a microscope. For example, a plate containing all the elements of the present device can be attached to a microscope in such a way that the laser beam, once it has passed the displacement means, is inserted into the optical path that passes through the objective of said microscope.

A second aspect of the present invention is directed to a procedure of determining surface roughness frequency using the above device. To do this, as described above, the ground glass plate is interposed in the path of the laser beam at the same time it rotates, so that the angle of illumination on the sample changes without the need to modify the position of the laser source. Thus, by correlating the light backscattered by the sample when it is illuminated by the different patterns produced by the ground glass as it rotates, the value of the correlation will be related to the roughness of the surface. On smoother surfaces, the correlation will hold, even for large angles of rotation. On the contrary, rougher surfaces will lose the correlation, even for small angles of rotation. Surface roughness can be indicative of changes in cell arrangement and tissue hydration, which may be indicative of some pathology or abnormal development of a tissue area.

Thus, the procedure to obtain the roughness frequency of the sample surface comprises the following steps:

1. Arranging the displacement means so that the ground glass plate is located within the path of the laser beam towards the surface as it rotates.
2. Emitting a laser beam that, after passing through the rotating ground glass plate, falls on the surface of the sample.
3. Receiving the light scattered in reflection by the surface during a complete rotation of the ground glass plate.

4. Determining the roughness frequency ($\rho_\theta$) from the received light intensity (I) and the angle of rotation of the ground glass plate ($\theta$) using the following formula:

$$\rho_\theta^{-1} \sim \frac{-\ln(C_{roughness}(\theta))}{\theta}$$

wherein $$C_{roughness}(\theta) \approx \frac{\langle I(\theta=0) \cdot I(\theta) \rangle}{\langle I(\theta=0)^2 \rangle} - 1.$$

A third aspect of the invention is directed to a procedure for determining the degree of depolarization of the surface using the above device. In effect, as described above, the half wave blade is interposed in the path of the laser beam at the same time that it rotates. Thus, the electromagnetic field of the emitted laser beam rotates depending on the angle of rotation of the half wave blade, thus rotating its plane of polarization. This allows analysis of the polarization anisotropy of the sample. To do this, measurements are taken for a complete rotation of the half wave blade and, then the autocorrelation of the measured intensity as a function of the angle of rotation of the half wave blade is calculated. The degree of depolarization finally obtained represents a measure of the polarization anisotropy of the sample. Certain tissues, such as muscle, have a high anisotropy. In these cases, part of the backscattered light maintains a direct relationship with the polarization of the incident beam. Changes in the cellular configuration of the sample, such as due to abnormal tissue growth, can thus be reflected in the value of the degree of depolarization obtained.

Thus, the procedure to obtain the degree of depolarization of the sample surface comprises the following steps:
1. Arranging the displacement means so that the half wave blade is located within the path of the laser beam towards the surface as it rotates.
2. Emitting a laser beam that, after passing through the rotating half wave blade, falls on the surface of the sample.
3. Receiving the light scattered in reflection by the surface during a complete rotation of the half wave blade.
4. Determining the degree of depolarization ($\delta P_\theta$) from the received light intensity (I) and the angle of rotation of the half wave blade ($\theta_p$) using the following formula:

$$\delta P_\theta^{-1} \sim \left( \frac{-\ln(C_{polarization}(\theta_p))}{\theta_p} \right)$$

wherein $$C_{polarization}(\theta_p) \approx \frac{\langle I(\theta_p=0) \cdot I(\theta_p) \rangle}{\langle I(\theta_p=0)^2 \rangle} - 1.$$

A fourth aspect of the invention is directed to a procedure for determining the average speed of tissue dispersive components using the device of the invention. In this case, the laser beam that reaches the surface of the sample must have characteristics that are invariant over time, so that neither the rotating ground glass plate nor the rotating half wave blade are placed in the path of the laser beam, or, in any case, the half wave blade in a fixed non-rotating position. The measurements thus obtained are temporal correlation measurements that allow in-vivo dynamic information to be obtained. To do this, the temporal autocorrelation of the light intensity measured as a function of time is performed to then obtain the parameter that measures the speed of the dispersive components of the tissue. This speed will allow inferring information about aspects such as cell motility or blood flow.

Thus, the procedure to obtain the average speed of the dispersive components of a fabric comprises the following steps:
1. Arranging the displacement means so that neither the half wave blade and the ground glass plate are in the path of the laser beam to the surface, or the half wave blade is located in a fixed position not rotary. In any case, the characteristics of the laser beam which falls on the surface are constant.
2. Emitting a laser beam which falls on the surface.
3. Receiving the light scattered in reflection by the surface during a time interval.
4. Determining the average speed of the dispersive components of the surface ($v_{dynamic}$) from the received light intensity (I) and time (t) using the following formula:

$$\langle v_{dynamic} \rangle \sim \left( \frac{-\ln(C_{dynamic}(t))}{t} \right)$$

wherein $$C_{dynamic}(t) \approx \frac{\langle I(0) \cdot I(r) \rangle}{\langle I(0)^2 \rangle} - 1$$

The measurement of these parameters will allow the creation of multidimensional maps of the dispersion of the analyzed tissue sample that will provide a large amount of information on its morphological and dynamic characteristics that will be useful for various applications.

PREFERRED EMBODIMENT OF THE INVENTION

The present invention will now be described with reference to the accompanying figures, which show various exemplary configurations of devices for characterizing the roughness profile of a tissue sample.

General Description

Figure 1:
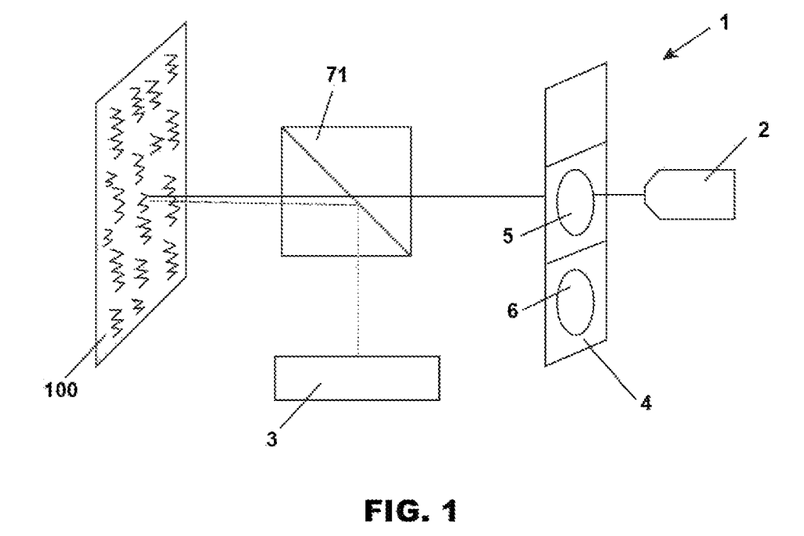
FIG. 1 shows a simplified diagram of the device according to the present invention.
Figure 2:
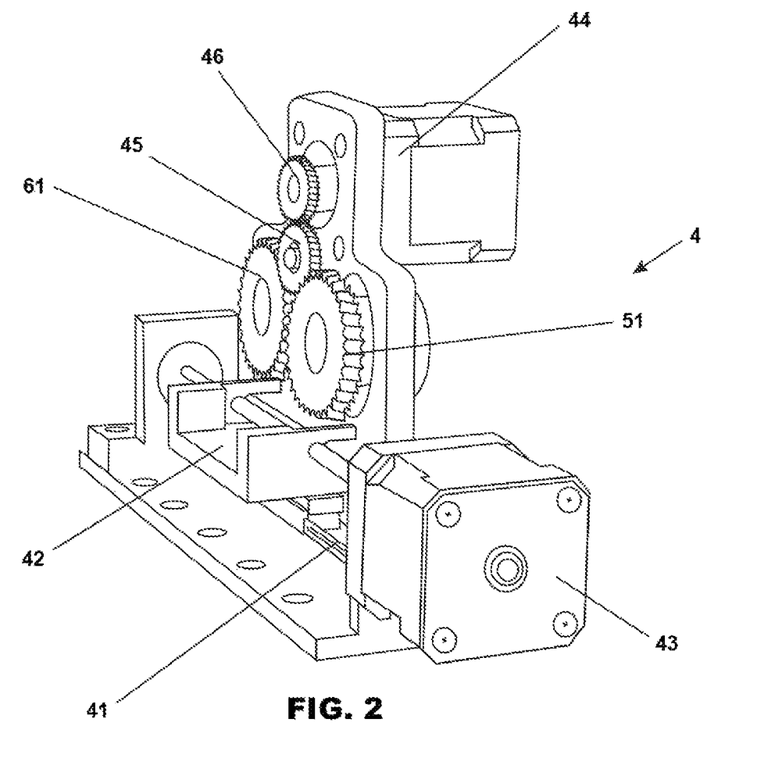
FIG. 2 shows a perspective view of an example of displacement means according to the present invention.
Figure 3:
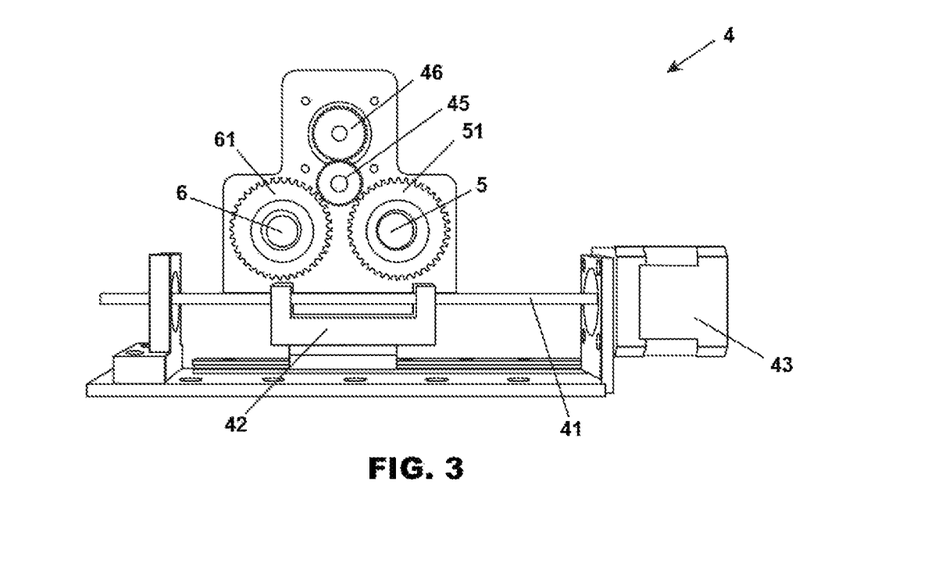
FIG. 3 shows a front view of the example of displacement means according to the present invention.
Figure 4:
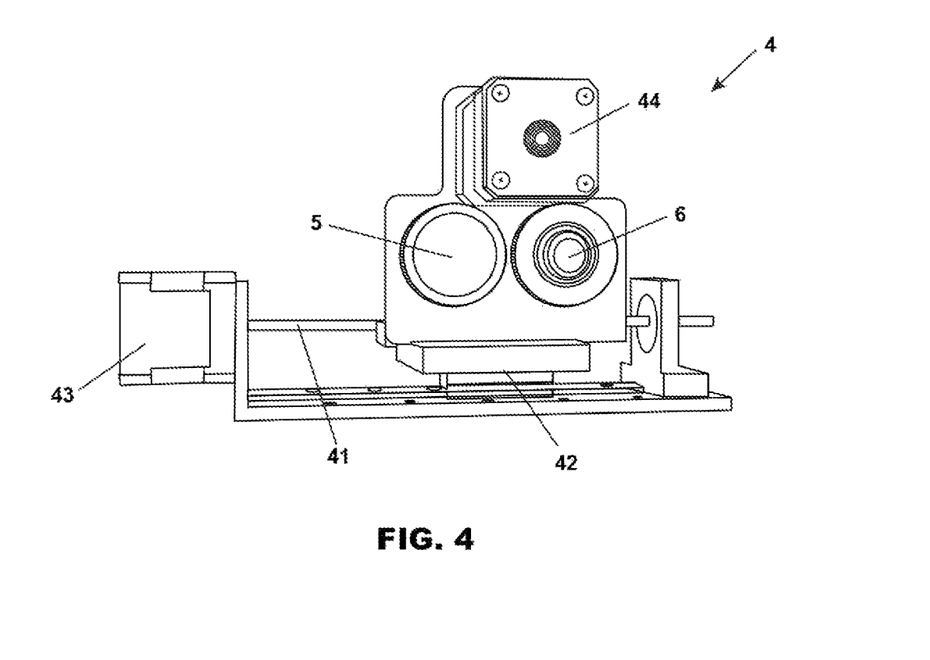
FIG. 4 shows a rear view of the example of displacement means according to the present invention.

FIG. 1 shows a simplified diagram of the device (1) of the present invention wherein the most important components have been represented. A laser source (2), which in this example is a 635 nm continuous wave laser, emits a laser beam directed towards the surface (100) of the tissue to be studied. Within the path of the laser beam towards the surface (100), a displacement means (4) is interposed that has at least one ground glass plate (5) and a half wave blade (6). The displacement means (4) can alternate between a first position wherein the laser beam passes through the ground glass plate (5), a second position wherein the laser beam passes through the half wave blade (6), and a third position wherein the laser beam does not pass through any of the two. That is, in the third position, the laser beam is not affected by its passage through the displacement means (4).

The laser beam continues its path, passing through a beam splitter (71) until it falls on the surface (100). The reflected light is diffuse due to the scattering phenomenon produced in the light wave due to the roughness of the sample. As a consequence, light is reflected according to multiple angles instead of just one. Part of this scattered light in reflection hits the beam splitter (71) again and is directed towards a photodetector (3). The signal from the photodetector (3) is subsequently directed towards a processing means (not shown in the figures), wherein it is analyzed according to the procedures described previously in this document.

FIGS. 2 to 5 show in greater detail an example of displacement means (4). In this configuration, the displacement means (4) comprises a guide (41) that takes the form of a threaded cylindrical rod arranged essentially perpendicularly in front of the laser source (2). A frame (42) is slidably coupled to the guide (41) so that it can slide along it from one end to the other. In this example, the frame (42) has two aligned holes through which the guide (41) passes. A translation motor (43) coupled to one end of the guide (41) causes rotation in one direction or another. Thus, when the guide (41) rotates around its own axis, the thread forces the frame (42) to move along it in one direction or another.

On the frame (42) there is arranged a body to which two gears are rotatably fixed: a first toothed wheel (51) provided with a central hole in which a ground glass (5) is fixed; and a second toothed wheel (61) provided with a central hole in which a half wave blade (6) is fixed. Thus, when the first or second toothed wheels (51, 61) rotate relative to the frame body (42), the ground glass (5) also rotates or the corresponding half wave blade (6). Both the first and second toothed wheels (51, 61) are coupled to a drive toothed wheel (46) through a further intermediate toothed wheel (45). The drive toothed wheel (46) is driven by a rotation motor (44). Thus, when the rotation motor (44) rotates, the rotation of the toothed wheel (46) rotates the intermediate toothed wheel (45) which, in turn, causes the rotation of the first and second toothed wheels (51, 61).

Thus, the operation of this displacement means (4) is as follows. Depending on the analysis procedure of the surface (100) to be carried out, the ground glass plate (5), the half wave blade (6), or neither of the two, is arranged in the path of the laser beam towards the surface (100). To do this, the translation motor (43) is activated until the desired element is placed in front of the laser source (2). Next, or at the same time, if necessary, the rotation motor (44) is activated to cause the rotation of the ground glass plate (5) or the half wave blade (6).

Example for Microscope

Figure 5:
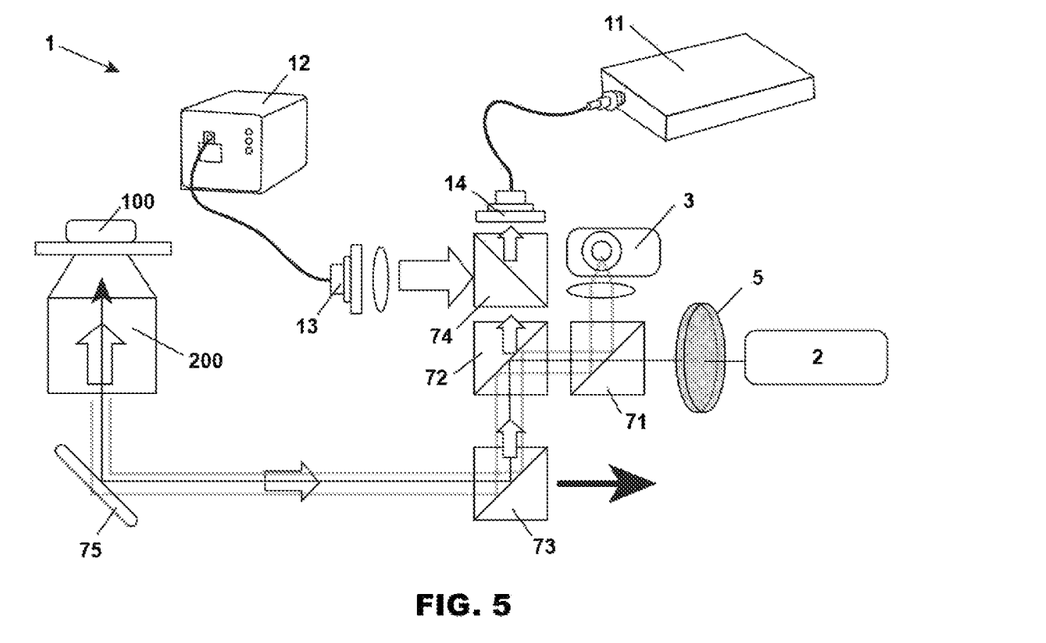
FIG. 5 shows a schematic view of the system of the invention implemented for a microscope.

FIG. 5 shows an example of a system (1) according to the present invention that can be configured for use in combination with a microscope (200). In this example, the displacement means (4) is arranged according to the first position, that is, with the ground glass plate (5) arranged in front of the laser source (2), and with a rotation motor (44) working. Thus, the laser beam passes through the rotating ground glass plate (5). The laser beam then passes through a beam splitter (71) and onto a dichroic filter (72) that reflects wavelengths above 620 nm and transmits wavelengths between 400 nm and 620 nm. The 635 nm laser beam is therefore reflected by the dichroic filter (72) and continues to a second beam splitter (73), which reflects it and sends it to a mirror (75), which finally orients it in parallel to the microscope objective (200). The laser beam falls on the surface (100), and the backscattered light follows the reverse path, passing through the mirror (75) and the beam splitter (73) and the dichroic filter (72) until it reaches the beam splitter (71), which reflects it towards the photodetector (3). Subsequently, through a processing means that is not shown in the figures, the analysis of the light intensity received by the photodetector (3) is carried out to obtain the described parameters.

The system shown in FIG. 5 further includes a series of additional elements, such as a spectrometer (11), a white light source (12) and collimators (13, 14). These elements are related to a series of measurements that are carried out in this system outside the object of the present invention, and therefore their operation is not described in detail here.

Example for Fiber Optics

Figure 6:
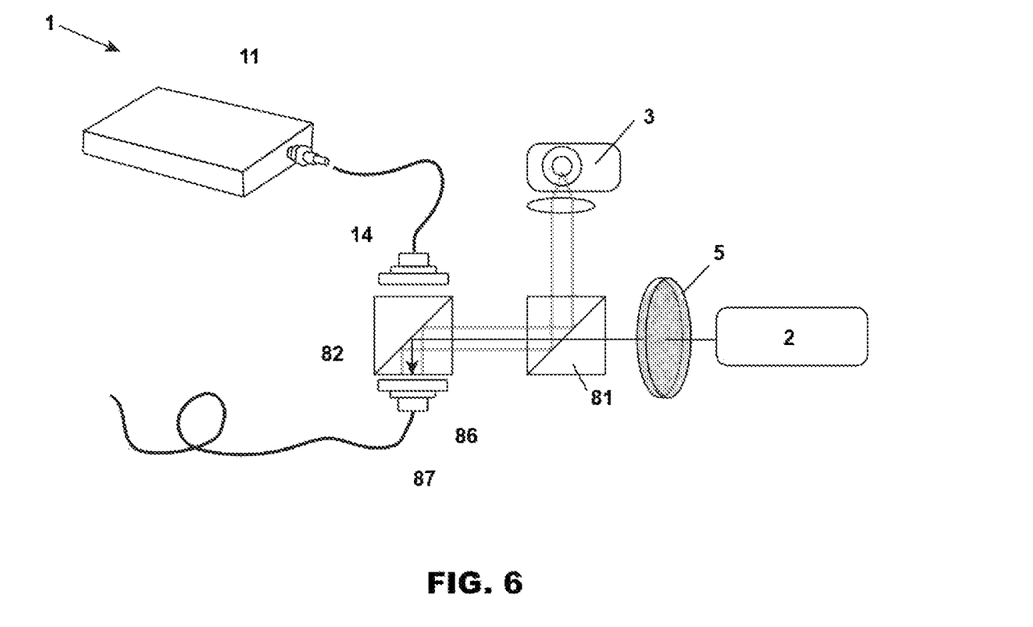
FIG. 6 shows a schematic view of the system of the invention implemented for an endoscope.

FIG. 6 shows another example of a system (1) according to the present invention, although in this case designed for use with an optical fiber (87). This configuration would be useful, for example, by arranging the optical fiber in an endoscope, which would allow the analysis of surfaces located inside a patient in-vivo. In this example, the displacement means (4) is also arranged in the first position, that is, with the ground glass plate (5) arranged in front of the laser source (2), and with the rotation motor (44) in operation. The laser beam thus passes through the beam splitter (81) and reaches a dichroic filter (82) that reflects wavelengths above 620 nm and transmits wavelengths between 400 nm and 620 nm. The laser beam is thus directed into an optical fiber (87) that will take it to the study surface (100) inside the patient. The light backscattered by the surface (100) will return along the same path until it reaches the beam splitter (81), which in this case will reflect it, directing it towards the photodetector (3). Subsequently, through a processing means that is not shown in the figures, the analysis of the light intensity received by the photodetector (3) is carried out to obtain the described parameters.

This system (1) further includes, as in the previous case, a spectrometer (11) and a collimator (14), used to carry out measurements outside the object of the present invention.

Analysis Procedures

The three procedures for obtaining surface characteristics described in this document are described below.

1. Speckle Interferometry Correlation Measurements

The speckle interferometry correlation measurements are made by making the laser beam pass through the ground glass (5) at the same time that it rotates, which will cause changes in the lighting pattern on the sample. The light intensity data backscattered by the sample is collected by the photodetector (3) and analyzed by the processing means so that the correlation of the light reflected by the sample when illuminated by the different patterns produced by the rotating glass is obtained. This correlation is related to the roughness of the surface: on very smooth surfaces the correlation will hold even for large angles of rotation, while on very rough surfaces the correlation will be lost even for small angles of rotation.

The correlation is calculated according to the following equation, wherein θ represents the angle of rotation of the ground glass and I(θ) is the light intensity received by the photodetector.

$$C_{roughness}(\theta) \approx \frac{\langle I(\theta=0) \cdot I(\theta) \rangle}{\langle I(\theta=0)^2 \rangle} - 1$$

The degree of roughness is calculated by adjusting $-\ln(c_{roughness}(\theta))$ as a function of the angle $\theta$, the slope of which is inversely related to the rate of variation of surface roughness. The parameter finally obtained is the "roughness frequency" ($\rho_\theta$).

$$\rho_\theta^{-1} \sim \frac{-\ln(C_{roughness}(\theta))}{\theta}$$

2. Depolarization Correlation Measurements

The depolarization correlation measurements are made by making the laser beam pass through the half wave blade (6) at the same time that it rotates. In this way, the incident electromagnetic field is rotated to later compare it with other previous positions of the half wave blade. This measurement offers very useful information on the degree of anisotropy of the fabric, since it compares the different states of polarization of the transmitted and reflected beam. Measurements are taken angularly for one full rotation of the half wave blade. Once performed, the autocorrelation of the measured intensity is calculated as a function of the angle of rotation ($\theta$) of the half wave blade (6).

$$C_{polarization}(\theta) \approx \frac{\langle I(\theta=0) \cdot I(\theta) \rangle}{\langle I(\theta=0)^2 \rangle} - 1$$

To obtain information on the level of depolarization, an adjustment of $-\ln(c_{polarization}(\theta))$ is made as a function of the angle of rotation ($\theta$) of the half wave blade. The slope of this fit is inversely proportional to the depolarization of the sample. This parameter is called the "degree of depolarization" ($\delta P_\theta$).

$$\delta P_\theta^{-1} \sim \left( \frac{-\ln(C_{polarization}(\theta))}{\theta} \right)$$

It should be noted that, in the case of implementation as a module for an endoscope, the optical fiber used will be multimode, which implies that the polarization can vary uncontrollably when crossing the fiber. However, this variation will have the same autocorrelation when rotating the incident polarization. Therefore, these measurements are not equivalent to the polarization measurements that have typically been made with single-mode fibers with maintained polarization, although equivalent quantitative results are obtained when performing autocorrelation.

3. Temporal Correlation Measurements

Temporal correlation measurements are made by ensuring that the laser beam that reaches the surface of the tissue has optical characteristics that are invariant over time. To do this, a first possibility consists of moving both the ground glass plate (5) and the half wave blade (6) out of the path of the laser beam. Alternatively, it is possible to place the half wave blade (6) in the path of the laser beam as long as it remains stationary. This possibility can be useful for applications with space problems, since in this case the displacement means (4) only requires two positions. Temporal correlation measurements allow in-vivo dynamic information to be obtained, such as cell motility and blood flow. For this, the temporal autocorrelation of the intensity (I) measured as a function of time (t) is performed.

$$C_{dynamic}(t) \approx \frac{\langle I(0) \cdot I(t) \rangle}{\langle I(0)^2 \rangle} - 1$$

Then, using the slope of the curve resulting from the adjustment of $-\ln(c_{dynamic}(t))$ as a function of time, the parameter that measures the average speed of the dispersive components of the tissue is obtained ($v_{dynamic}$).

$$\langle v_{dynamic} \rangle \sim \left( \frac{-\ln(C_{dynamic}(t))}{t} \right)$$

The joint measurement of the parameters measured thanks to the device (1) of the present invention will allow the creation of multidimensional maps of the dispersion of the analyzed tissue sample that will provide a large amount of information on its morphological and dynamic characteristics in the face of various applications.

What is claimed is:

1. A device for characterizing a rough profile of a tissue sample, comprising:
    a laser source that illuminates the surface of the tissue sample with a continuous wave laser beam;
    a photodetector that receives the light scattered in reflection by the surface of the tissue sample illuminated by the laser beam; and
    a structure that comprises:
        a guide arranged in front of the laser source perpendicular to the emitted laser beam;
        a frame movable along the guide, the ground glass plate and the half wave blade being coupled to said frame:
        a translation motor configured to move the frame along the guide to selectively place the ground glass plate, the half wave blade in the path of the laser beam, or neither the ground glass plate nor the half wave blade are positioned in the path of the laser beam; and
        a rotation motor coupled to the ground glass plate and the half wave blade to rotate respectively the ground glass plate and the half wave blade when the ground glass plate and the half wave blade are in front of the laser source, wherein the structure is configured to alternate between:
        a first position wherein a rotating ground glass plate is disposed within a path of the laser beam towards the surface;
        a second position wherein a rotating half wave blade is disposed within the path of the laser beam towards the surface; and
        a third position wherein neither the ground glass plate nor the half wave blade are arranged within the path of the laser beam towards the surface, or the half wave blade is in a fixed non-rotating position.

2. The device according to claim 1, wherein the ground glass plate is fixed to a first toothed wheel and the half wave blade is fixed to a second toothed wheel, and wherein the rotation motor is coupled to said first and second toothed wheels to rotate them.

3. The device according to claim 1, further comprising mirrors, lenses and/or beam splitters that conduct the laser beam from the laser source towards the surface of the tissue sample and the light scattered in reflection by the surface of the tissue sample towards the photodetector.

4. The device according to claim 1, further comprising an optical fiber housed in an endoscope that conducts the laser beam from the laser source towards the surface of the tissue sample and the light scattered in reflection by the surface of the tissue sample towards the photodetector.

5. The device according to claim 1, further comprising an external processor, wherein a software is used to receive a signal obtained by the photodetector in response to the light reflected in a received dispersion and calculate parameters for characterizing the rough profile of the surface of the tissue sample.

6. The device according to claim 5, wherein the parameters are selected from the group consisting of a roughness frequency, a degree of depolarization, an average speed of dispersive components of the tissue sample examined.

7. The device according to claim 1, which has a wavelength of less than 635 nm.

8. The device according to claim 1, coupled to a microscope.

9. A procedure for determining the roughness frequency of a surface using the device of claim 1, comprising:
arranging the structure so that the ground glass plate is located within the path of the laser beam towards the surface at the same time as it rotates;
emitting a laser beam which, after passing through the rotating ground glass plate, falls on the surface;
receiving the light scattered in reflection by the surface during a complete rotation of the ground glass plate;
determining the roughness frequency ($p_\theta$) from the received light intensity (I) and the angle of rotation ($\theta$) of the ground glass plate using the following formula:

$$\rho_\theta^{-1} \sim \frac{-\ln(C_{roughness}(\theta))}{\theta}$$

wherein $$C_{roughness}(\theta) \approx \frac{\langle I(\theta=0) \cdot I(\theta) \rangle}{\langle I(\theta=0)^2 \rangle} - 1.$$

10. A procedure for determining the degree of depolarization of a surface using the device of claim 1, comprising:
arranging the structure so that the half wave blade is located within the path of the laser beam towards the surface at the same time as it rotates;
emitting a laser beam which, after passing through the rotating half wave blade, falls on the surface;
receiving the light scattered in reflection by the surface during a complete rotation of the half wave blade;
determining the degree of depolarization ($\delta P_\theta^{-1}$) from the received light intensity (I) and the angle of rotation ($\theta_p$) of the half wave blade using the following formula:

$$\delta P_\theta^{-1} \sim \left( \frac{-\ln(C_{polarization}(\theta_p))}{\theta_p} \right)$$

wherein $$C_{polarization}(\theta_p) \approx \frac{\langle I(\theta_p=0) \cdot I(\theta_p) \rangle}{\langle I(\theta_p=0)^2 \rangle} - 1.$$

11. A procedure for determining the average speed of the dispersive components of the tissue sample using the device of claim 1, comprising:
arranging the structure so that in the path of the laser beam towards the surface there is none of the half wave blade and the ground glass plate, or the half wave blade is located in a fixed non-rotating position;
emitting a laser beam which falls on the surface;
receiving the light scattered in reflection by the surface during a time interval;
determining the average speed of the dispersive components ($V_{dynamic}$) of the surface from the received light intensity (I) and the time (t) using the following formula:

$$\langle v_{dynamic} \rangle \sim \left( \frac{-\ln(C_{dynamic}(t))}{t} \right)$$

wherein $$C_{dynamic}(t) \approx \frac{\langle I(0) \cdot I(r) \rangle}{\langle I(0)^2 \rangle} - 1.$$

* * * * *

UNITED STATES PATENT AND TRADEMARK OFFICE
CERTIFICATE OF CORRECTION

PATENT NO. : 12,264,911 B2
APPLICATION NO. : 17/906143
DATED : April 1, 2025
INVENTOR(S) : Roberto Fernández Fernández It is certified that error appears in the above-identified patent and that said Letters Patent is hereby corrected as shown below:

In the Specification

Column 6, Line 26-29, delete "$C_{dynamic}(t) \approx \frac{\langle I(0) \cdot I(r) \rangle}{\langle I(0)^2 \rangle} - 1$" and insert -- $C_{dynamic}(t) \approx \frac{\langle I(0) \cdot I(t) \rangle}{\langle I(0)^2 \rangle} - 1$ --.

In the Claims

Column 10, Claim 1, Line 33, delete "said frame: a" and insert -- said frame; a --.

Column 12, Claim 11, Line 36-39, delete "$C_{dynamic}(t) \approx \frac{\langle I(0) \cdot I(r) \rangle}{\langle I(0)^2 \rangle} - 1.$" and insert -- $C_{dynamic}(t) \approx \frac{\langle I(0) \cdot I(t) \rangle}{\langle I(0)^2 \rangle} - 1.$ --.

Signed and Sealed this
Twelfth Day of August, 2025

Coke Morgan Stewart
*Acting Director of the United States Patent and Trademark Office*